(12) United States Patent
Kibler et al.

(10) Patent No.: US 11,116,974 B2
(45) Date of Patent: Sep. 14, 2021

(54) DEVICE AND METHOD FOR MULTI-MODALITY SPINAL CORD STIMULATION THERAPY

(71) Applicant: BIOTRONIK SE & CO. KG, Berlin (DE)

(72) Inventors: Andrew B. Kibler, Lake Oswego, OR (US); Dirk Muessig, West Linn, OR (US); Marcelo Baru, Tualatin, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 227 days.

(21) Appl. No.: 15/924,382

(22) Filed: Mar. 19, 2018

(65) Prior Publication Data

US 2018/0272133 A1     Sep. 27, 2018

Related U.S. Application Data

(60) Provisional application No. 62/476,884, filed on Mar. 27, 2017, provisional application No. 62/590,394, filed on Nov. 24, 2017.

(51) Int. Cl.
*A61N 1/36* (2006.01)
*A61N 1/05* (2006.01)

(52) U.S. Cl.
CPC ....... *A61N 1/36062* (2017.08); *A61N 1/0502* (2013.01); *A61N 1/0553* (2013.01);
(Continued)

(58) Field of Classification Search
CPC ............... A61N 1/0502; A61N 1/0553; A61N 1/36017; A61N 1/36021; A61N 1/36031;
(Continued)

(56) References Cited

U.S. PATENT DOCUMENTS

| 8,965,516 B2 | 2/2015 | Bennett et al. |
| 9,278,215 B2 | 3/2016 | Thacker et al. |

(Continued)

FOREIGN PATENT DOCUMENTS

| WO | 2013036880 A1 | 3/2013 |
| WO | 2013134725 A1 | 9/2013 |
| WO | 2014093964 A1 | 6/2014 |

*Primary Examiner* — Christopher A Flory
(74) *Attorney, Agent, or Firm* — Laurence A. Greenberg; Werner H. Stemer; Ralph E. Locher

(57) ABSTRACT

A device for neurostimulation includes a pulse generator for generating current having pulses and at least one first pair of electrodes connected to the pulse generator. The device provides a user-programmable therapy strength parameter configuration and at least two current parameter configurations for neurostimulation stored in the pulse generator. The current parameter configurations are controlled by the therapy strength configuration, at least one of the current parameter configurations is associated with a level of paresthesia sensation of a patient and at least one of the current parameter configurations is associated with a paresthesia-free therapy for the patient. The association between therapy strength parameter and current parameter configurations uniquely adjusts the current parameter configurations based on paresthesia or paresthesia-free intent, when neurostimulation is performed using parameter configurations. Particularly, the current parameter configurations include parameters such as pulse trains, pulse frequencies, duty cycling, and amplitudes of the current.

17 Claims, 3 Drawing Sheets

(52) U.S. Cl.
CPC ..... *A61N 1/36017* (2013.01); *A61N 1/36021* (2013.01); *A61N 1/36031* (2017.08); *A61N 1/36034* (2017.08); *A61N 1/36057* (2013.01); *A61N 1/36071* (2013.01); *A61N 1/36132* (2013.01); *A61N 1/36157* (2013.01); *A61N 1/36171* (2013.01); *A61N 1/36175* (2013.01); *A61N 1/36178* (2013.01); *A61N 1/36164* (2013.01)

(58) Field of Classification Search
CPC ............ A61N 1/36034; A61N 1/36057; A61N 1/36062; A61N 1/36132; A61N 1/36157; A61N 1/36164; A61N 1/36171; A61N 1/36175; A61N 1/36178
USPC .......................................................... 607/46
See application file for complete search history.

(56) References Cited

U.S. PATENT DOCUMENTS

| | | | |
|---|---|---|---|
| 9,333,358 B2 * | 5/2016 | Alataris | A61N 1/36182 |
| 9,333,360 B2 * | 5/2016 | Alataris | A61N 1/0551 |
| 9,409,019 B2 * | 8/2016 | Walker | A61N 1/36071 |
| 9,421,366 B2 | 8/2016 | Tyler et al. | |
| 9,833,614 B1 * | 12/2017 | Gliner | A61N 1/36062 |
| 9,895,539 B1 * | 2/2018 | Heit | A61N 1/36071 |
| 9,981,131 B2 * | 5/2018 | Kent | A61N 1/36132 |
| 9,993,645 B2 * | 6/2018 | Walker | A61N 1/36167 |
| 10,149,978 B1 * | 12/2018 | Park | A61N 1/36157 |
| 10,220,208 B2 * | 3/2019 | Alataris | A61N 1/0553 |
| 10,226,628 B2 * | 3/2019 | Khalil | A61N 1/36071 |
| 10,328,256 B1 * | 6/2019 | Gliner | A61N 1/36062 |
| 10,413,729 B2 * | 9/2019 | Parker | A61N 1/36157 |
| 10,500,399 B2 * | 12/2019 | Single | A61N 1/36071 |
| 10,556,112 B1 * | 2/2020 | Park | A61N 1/36062 |
| 10,569,088 B2 * | 2/2020 | Dinsmoor | A61N 1/0551 |
| 10,569,089 B1 * | 2/2020 | Park | A61N 1/36171 |
| 10,576,286 B1 * | 3/2020 | Park | A61N 1/36175 |
| 2010/0274312 A1 | 10/2010 | Alataris et al. | |
| 2010/0274318 A1 * | 10/2010 | Walker | A61N 1/36021 607/46 |
| 2013/0066411 A1 * | 3/2013 | Thacker | A61N 1/06 607/117 |
| 2013/0204323 A1 * | 8/2013 | Thacker | A61N 1/36171 607/46 |
| 2013/0204324 A1 * | 8/2013 | Thacker | A61N 1/0558 607/46 |
| 2013/0261695 A1 * | 10/2013 | Thacker | A61N 1/0551 607/46 |
| 2013/0261696 A1 * | 10/2013 | Thacker | A61N 1/36075 607/46 |
| 2014/0296936 A1 * | 10/2014 | Alataris | A61N 1/36132 607/46 |
| 2014/0379044 A1 * | 12/2014 | Walker | A61N 1/0551 607/46 |
| 2015/0005842 A1 | 1/2015 | Lee et al. | |
| 2015/0328465 A1 * | 11/2015 | Tyler | A61N 1/36139 607/62 |
| 2016/0074664 A1 * | 3/2016 | De Ridder | A61N 1/36185 607/59 |
| 2016/0082261 A1 | 3/2016 | Moffitt et al. | |
| 2016/0129272 A1 * | 5/2016 | Hou | A61N 1/37241 607/62 |
| 2017/0143971 A1 * | 5/2017 | Kent | A61N 1/36132 |
| 2017/0209702 A1 * | 7/2017 | Lee | A61N 1/36164 |
| 2017/0239478 A1 * | 8/2017 | Parker | A61N 1/36171 |
| 2017/0246456 A1 * | 8/2017 | Tyler | A61N 1/0551 |
| 2017/0291029 A1 * | 10/2017 | Khalil | A61N 1/36071 |
| 2018/0028815 A1 * | 2/2018 | Moffitt | A61N 1/36071 |
| 2018/0236237 A1 * | 8/2018 | Kent | A61N 1/36132 |
| 2018/0333578 A1 * | 11/2018 | Mock | A61N 1/37264 |
| 2018/0369592 A1 * | 12/2018 | Johanek | A61N 1/3606 |
| 2019/0175904 A1 * | 6/2019 | Baru | A61N 1/36128 |
| 2019/0344083 A1 * | 11/2019 | Marnfeldt | A61N 1/36125 |
| 2020/0001096 A1 * | 1/2020 | Zhang | A61F 7/12 |
| 2020/0046987 A1 * | 2/2020 | Cantua | A61N 1/36071 |
| 2020/0061380 A1 * | 2/2020 | Zhang | A61N 1/0476 |

* cited by examiner

DEVICE AND METHOD FOR MULTI-MODALITY SPINAL CORD STIMULATION THERAPY

CROSS-REFERENCE TO RELATED APPLICATION

This application claims the benefit, under 35 U.S.C. § 119, of U.S. Provisional Patent Application No. 62/476,884, filed Mar. 27, 2017, and U.S. Provisional Patent Application No. 62/590,394, filed Nov. 24, 2017; the prior applications are herewith incorporated by reference in their entirety.

BACKGROUND OF THE INVENTION

Field of the Invention

Traditional paresthesia-based spinal cord stimulation (SCS) and recent high frequency paresthesia-free spinal cord stimulation are thought to differ in mechanism of action by academic and industry neuromodulation scientists due to recent preclinical and clinical evidence. While paresthesia-based stimulation allows for a patient to continuously titrate their therapy to suit their needs, that practice is rare during paresthesia-free stimulation, where the patient has little to no immediate feedback on how their adjustments will impact their pain relief.

On the market today exist systems which are able to deliver either high frequency/energy paresthesia free stimulation or low frequency paresthesia-based stimulation, however no available devices solve the problems of intuitive patient control and self-titration, and activation of both theorized pain relief mechanisms at the same time.

Spinal cord stimulation as a means of pain relief for patients suffering from neuropathic pain has traditionally been thought of as requiring paresthesia sensations to overlap a patient's region of pain in order to provide relief. Recent research has shown that an alternate mechanism of pain relief is available in which paresthesia-free stimulation is effective in patients after a 1-2 day delay.

Both therapies require adjustment and titration, with the first therapy requiring precise control of paresthesia location and thus stimulation parameters. The second, paresthesia-free therapy also can require lower resolution adjustment of stimulation location, with 1-2 days delay before maximum pain relief is achieved.

Both therapies are reported to be about 60-80% effective in patient populations at delivering at least 50% pain relief, with published instances of paresthesia therapy being successful when paresthesia-free therapy is not, and vice-versa. In addition, both therapies may lose efficacy over time, resulting in additional surgery required for device removal, replacement, or lead adjustment.

While 50% pain relief is a marked improvement of a patient's experience for either of these therapies, the clinical pain specialist field desires an improved SCS therapy that can consistently approach higher levels of efficacy. At the same time, the therapy must be simple for the patient to control and use, and provide a logical means of patient-directed titration.

Known solutions include:
HF-10 paresthesia-free therapy;
Paresthesia-based therapy with traditional remote-control user adjustment on an as-needed basis;
Multi-program therapies which provide the user a selection of four to eight unique stimulation programs, sometimes with paresthesia and sometimes without with which they can switch between to select their favorite;
Burst therapy (paresthesia-free in most patients).

HF-10 therapy provides very slow feedback (1-2 days), making adjustment difficult on activity-related pain timescales during the day. In addition, due to the fact that the stimulation doesn't generate any perceptible feedback to the patient he or she may question whether the therapy device is on or working at its optimal potential. Charging burden is directly related to the amplitude of stimulation, leading to the possibility that a patient may be recharging more often or for longer than they otherwise would need to because of this lack of feedback. The paresthesia-free state of the therapy and complex optimal amplitude criteria results in a therapy that the patient cannot titrate on a daily basis to track the daily increases and decreases of their pain related to activity and inflammation. If they attempt to do so, they risk running therapy at either a too high amplitude, outside the optimal range, or too low with the result being poorer pain management. Furthermore, the efficacy of this therapy leaves room for improvement, as does a reported 5% per year failure rate due to loss of efficacy.

Paresthesia-based therapy, while more rapidly acting, also suffers from drawbacks related to its patient population success rate, and long-term failure rate due to the fact that many patients dislike the chronic experience of paresthesia in their location(s) of pain for the rest of their lives.

Multi-program therapies are problematic due to complexities of use, with patients required to keep in mind that they must allow for 24-48 hours for pain relief when they switch to a paresthesia-free program, and less time for a paresthesia-based program. Furthermore, the optimal amplitude settings for a paresthesia-based program can be unintuitive for a patient to select on their own, as the optimal amplitude may be well below the paresthesia threshold for a particular stimulation therapy setting.

Burst therapy suffers from the same problems as HF-10 therapy for most patients, operating without any paresthesia. For patients for whom the amplitude is increased to provide pain relief with resulting paresthesia, it is not clear to users whether titration should increase amplitude for additional pain relief, or if a decrease in amplitude is required.

All of those existing solutions result in a sub-optimal state of the art of spinal neuromodulation for pain.

SUMMARY OF THE INVENTION

Based on the above, the problem to be solved by the present invention is to provide a device, a therapeutic program and an approach which improves on the efficacy of the current state of the art of neuromodulatory neuropathic pain relief, is simple to program and use, and is able to provide substantial pain relief for a broad population of patients suffering from lower back and leg pain. In addition, the solution should provide rapid feedback to the patient related to their therapy strength, and be controllable in a simple to use, patient-titratable interface.

The problem is solved by a device and a method according to the invention as described below. Preferred embodiments are stated in the sub claims and are described below.

According to the invention, a device for neurostimulation, particularly for pain relief, is provided, wherein the device comprises:
a pulse generator capable of generating a current having pulses, and at least one first pair of electrodes connected to the pulse generator, wherein the device provides at least one current parameter configuration for neurostimulation stored in the device, the current parameter configuration is programmable by a user, and the current parameter configuration is associated with a level paresthesia sensation of a patient, when the neurostimulation is performed by using the parameter configuration. Particularly, the current parameter configuration includes parameters such as pulse trains, pulse frequencies and amplitudes of the current.

According to an embodiment of the present invention, the pulse generator is capable of generating a current having pulses with a frequency in the range of 1 Hz to 100 kHz.

According to an embodiment of the present invention, a device for neurostimulation, particularly for pain relief, is provided, wherein the device comprises:

a pulse generator capable of generating current having pulses with frequencies in the range of 1 Hz to 100 kHz, and at least one first pair of electrodes connected to the pulse generator, wherein the device provides a user-programmable therapy strength parameter configuration and at least two current parameter configurations for neurostimulation stored in the pulse generator, the current parameter configurations being controlled by the therapy strength configuration, and wherein at least one of the current parameter configurations is associated with a level of paresthesia sensation of a patient and at least one of the current parameter configurations is associated with a paresthesia-free therapy for the patient, wherein the association between the therapy strength parameter and the current parameter configurations uniquely adjusts the current parameter configurations based on their paresthesia or paresthesia-free intent, and when the neurostimulation is performed using the parameter configurations. Particularly, the current parameter configurations include parameters such as pulse trains, pulse frequencies, duty cycling, and amplitudes of the current.

Advantageously, the device of the invention is a suitable device for neurostimulation, particularly for spinal cord stimulation for pain relief, wherein the device allows the application of interleaved low frequencies and high frequencies pulse trains to a patient with a predefined stimulation pattern. According to an aspect of the present invention, the low frequencies are paresthesia-inducing, wherein the high frequencies are sub-paresthesia and effectively pain-relieving stimulation frequencies. Thus, the device allows the patient to directly experience feedback from the neurostimulation, which enables the patient to titrate the needed therapy strength for achieving substantial pain relief. Particularly, the device of the invention is constructed to deliver the current with the above described low and high frequencies with an integrated dynamic amplitude program included within the current parameter configurations.

In certain embodiments, the device is implantable. In certain embodiments, the pulse generator is subcutaneously implantable. Particularly, the device of the invention is constructed for implantation in the supra-dural space of a patient's vertebral lumen. In certain embodiments, the pulse generator is rechargeable.

In certain embodiments, the at least one first pair of electrodes are constructed as percutaneous leads or paddle leads. Particularly, the at least one first pair of electrodes are constructed to be implanted in the patient's epidural space, wherein particularly the electrodes of the at least one first pair are in electrical contact with the dorsal column axons.

In certain embodiments, the current parameter configuration includes parameters for at least a first pulse train and a second pulse train, wherein the first pulse train includes pulses of duration and amplitude so as to not induce dorsal column depolarizations (paresthesia), particularly utilizing high frequency pulses having a frequency in the range of 200 Hz to 100 kHz, particularly in the range of 200 Hz to 20 kHz, and the second pulse train includes low frequency pulses of duration and amplitude so as to induce dorsal column depolarizations (paresthesia), particularly having a frequency in the range of 1 Hz to 200 Hz. Particularly, the device of the invention is constructed to deliver the low and high frequencies pulses substantially at the same time, particularly in the form of charge balanced trains of pulses.

In certain embodiments, the first pulse train has pulse amplitudes within a first range below the threshold of dorsal column activation, and the second pulse train has pulse amplitudes within a second range which exceeds the level required to activate dorsal columns.

In certain embodiments, the current parameter configuration includes a therapy strength scale adjustable by the user or the patient, wherein:

at the beginning of the therapy strength scale, the first pulse train is set on a first amplitude at the lower limit of the first range, and the second pulse train is set on a second amplitude at the lower limit of the second range, at the end of the therapy strength scale, the first amplitude is set on the upper limit of the first range, and the second amplitude is set on the upper limit of the second range, in a low strength range of the therapy strength scale, the second amplitude is maintained, and the first amplitude increase towards or to the upper limit of the first range; and in a high strength range of the therapy strength scale, the first amplitude is maintained at the upper limit of the first range, while the second amplitude is increased up to the upper limit of the second range, wherein an increase on the therapy strength scale, particularly within the high strength range, can be experienced by the patient as increasing paresthesia.

The skilled person will understand that within the high strength range the second amplitude increases from the lower limit of the second range or from a value between the lower and upper limit of the second range to the upper limit of the second range.

Advantageously, the patient receives a direct feedback from the device of the invention in terms of paresthesia, and optionally pain relief, and can experience the increasing therapy strength at sufficient strength settings. This allows the patient to adjust the therapy strength according to his/her needs.

Preferably, the lower limit of the second range is set in the current parameter configuration such that the patient experiences minimal paresthesia, particularly at a barely-perceptible level. Likewise, the upper limit of the second range is preferably set in current parameter configuration such that the patient can comfortably experience paresthesia at the maximum comfortable level. The upper limit of the second range is particularly suitable to prevent the patient from over-driving his or her paresthesia stimulation past the point of comfort.

The increase of the second amplitude, the amplitude of the low frequency pulses, is preferably experienced by the patient as increasing paresthesia. Furthermore, the first range is preferably set in the current parameter configuration such that the patient cannot experience paresthesia within the first range. More preferable, the lower limit of the first range is set in the current parameter configuration such that the patient experiences a minimum level of pain relief.

In certain embodiments, the therapy strength scale includes an intermediate (increasing) strength range between the low and high strength range of the therapy strength scale, in which the first amplitude increases towards the upper limit of the first range and the second amplitude increases towards the upper limit of the second range, wherein an increase in the intermediate range can be experienced by the patient as increasing paresthesia, which is further increased upon increase in the high strength range.

At the beginning of the intermediate (increasing) strength range, the second amplitude is preferably set on the lower limit of the second range, while the first amplitude is set between the lower and upper limit of the first range. Preferably, the patient experiences very good daily pain relief at the beginning of the intermediate strength range and a further increase within the intermediate strength range, wherein both the first and second amplitude being increased, can be experienced by the patient as increasing paresthesia preferably accompanied by increasing pain relief.

In certain embodiments, the therapy strength is remotely adjustable by the user or the patient. This is advantageous in cases, in which the device of the invention is implanted.

In certain embodiments, the first and second pulse trains are alternatingly delivered to the patient by the first pair of electrodes.

In certain embodiments, the device includes a second pair of electrodes connected to the pulse generator. Particularly, the second pair of electrodes is constructed for implantation in the supra-dural space of a patient's vertebral lumen, wherein particularly the electrodes of the second pair are in electrical communication with the dorsal column axons. In certain embodiments, the first impulse train is delivered to the patient by the first pair of electrodes, and the second pulse train is delivered to the patient by the second pair of electrodes. In certain embodiments, the first and second pulse trains are delivered simultaneously without overlapping.

According to the invention, a method for neurostimulation, particularly for pain relief, is provided, wherein the method comprises applying current pulses to the patient, particularly to the spinal cord of the patient, wherein:
the current pulses include
a first pulse train having high frequency pulses having a frequency with a first amplitude in a first range, and
a second pulse train having low frequency pulses having a frequency with a second amplitude in a second range, and
the current pulses are applied with an adjustable therapy strength setting, wherein
at a lowest strength, the first amplitude is set on the lower limit of the first range, and the second amplitude is set on the lower limit of the second range;
at a highest strength, the first amplitude is set on the upper limit of the first range, and the second amplitude is set on the upper limit of the second range;
at a low strength range, the second amplitude is maintained at the lower limit of the second range, and the first amplitude increases towards or up to the upper limit of the first range; and
at a high strength range, the first amplitude is maintained at the upper limit of the first range, while the second amplitude is increased up to the upper limit of the second range.

Preferably, according to an embodiment of the inventive method,
the current pulses comprises
a first pulse train having high frequency pulses having a frequency in the range of 200 Hz to 100 kHz with a first amplitude in a first range, in particular in the range of 200 to 20 kHz, and
a second pulse train having low frequency pulses having a frequency in the range of 1 Hz to 200 Hz with a second amplitude in a second range.

The method of the invention provides particularly a novel therapeutic stimulation approach, which combines both low and high frequency stimulation for pain relief. Advantageously, the therapy strength can be straightforwardly experienced by the patient by sensations of paresthesia preferably accompanied by increasing pain relief.

Particularly, the method of the invention can be performed with or executed by the device of the invention.

Preferably, the lower limit of the second range is set such that the patient experiences minimal paresthesia, particularly at a barely-perceptible level. Likewise, the upper limit of the second range is preferably set such that the patient can maximally but still comfortably experience paresthesia under low frequency stimulation. The increase of the second amplitude, the amplitude of the low frequency pulses, is preferably experienced by the patient as increasing paresthesia. Furthermore, the first range is preferably set such that the patient cannot experience paresthesia within the first range. More preferable, the lower limit of the first range is set in the current parameter configuration such that the patient experiences a minimum level of pain relief.

In certain embodiments, in an intermediate (increasing) therapy strength range between the low and high therapy strength ranges, the first amplitude increases towards the upper limit of the first range and the second amplitude increases towards the upper limit of the second range.

At the beginning of the intermediate (increasing) strength range, the second amplitude is preferably set on the lower limit of the second range, while the first amplitude is set between the lower and the upper limit of the first range. Preferably, the patient experiences very good daily pain relief at the beginning of the intermediate strength range, and a further increase of the therapy strength, wherein both the first and the second amplitude are increased, can be experienced by the patient as increasing paresthesia and preferably accompanied by increasing pain relief.

In certain embodiments, the therapy strength is adjusted by the patient. In certain embodiments, a therapy strength increase within the high strength range and/or the intermediate strength range is experienced by the patient as increasing paresthesia.

In certain embodiments, the currents are applied by an implantable pulse generator (IPG).

In certain embodiments, the first range and the second range are determined based on the experience of the patient, wherein the second range, the upper limit of the second range is preferably set such that the patient can comfortably experience paresthesia at the maximum comfortable level, the lower limit of the second range is set such that the patient experiences barely-perceptible paresthesia, and particularly the upper limit of the second range is set such that the patient still comfortably experiences paresthesia. Preferably, the device of the invention is implanted into the patient and the above named parameters are determined as described above.

In certain embodiments, the therapy strength is adjusted by the patient.

Particularly disclosed herein is a device, a therapy and method for spinal cord stimulation (SCS) and control of the same which activates multiple mechanisms of pain relief while allowing the user to adjust their therapy in a simple manner which transparently titrates the mechanisms to suit their needs. This is accomplished via a novel abstracted 'therapy strength' patient setting which transparently derives stimulation parameters of multiple therapy modalities as programmed and titrated by a clinician, such that the therapy is optimized through the patient's control without the patient having to understand fine details of the underlying therapy mechanisms. The disclosed therapy combines sub-paresthesia stimulation at amplitude $A_1$, interleaved with pulses of a lower frequency at a second amplitude $A_2$. For instance, a stimulation regime can be chosen according to U.S. Provisional Application No. 62/476,885 which is incorporated herein by reference in its entirety. The user adjusts their therapy via a single therapy strength-setting control within a range such that at low desired therapy levels, $A_2$ is at a minimum value and adjustments primarily adjust amplitude $A_1$. At intermediate ranges of desired therapy level, $A_2$ and $A_1$ are scaled within a preset range, and at high desired therapy strengths, $A_2$ is increased further once $A_1$ has reached its maximum, permitting maximum combined effect from both mechanisms of pain relief.

A benefit of this invention is an improved pain therapy beyond the state of the art by giving control and feedback back to the patient and by leveraging both pain relief mechanisms of paresthesia and sub-paresthesia methodologies for maximum effect.

A rechargeable implantable pulse generator (IPG) is implanted in a patient's lower back subcutaneously, with percutaneous or paddle leads running from the IPG to the supra-dural space in a patient's spinal column. After implantation, the patient's perception levels at $LF(A_2)$ and $HF(A_1)$ are determined and the stimulation limits $LL_1$, $UL_1$, $LL_2$, and $UL_2$ are set, such that the patient cannot perceive paresthesia due to $HF(A_1)$ stimulation within the range $LL_1$-$UL_1$, and the patient can perceive paresthesia due to $LF(A_2)$ stimulation beginning within the range $LL_2$-$UL_2$. Furthermore, $LS_1$, $UL_1$, $LS_2$, $US_2$ are set such that $LS_1$ substantially begins at the lowest range of the patients therapy strength, $LS_2$ and $US_1$ are within the patient's therapy range, and $US_2$ is at the top end of the patient's therapy strength range. When the therapy strength setting is below $LS_1$ or $LS_2$, the corresponding pulse amplitude for that pulse train is the lower of either: LLx of the waveform, or the amplitude of the other waveform, whichever is lower.

This combination of preferred parameters enables a combination of $HF(A_1)$ and $LF(A_2)$ stimulation such that it is apparent to the user when they increase stimulation amplitude that additional therapy is felt, as the $LF(A_2)$ paresthesia amplitude increases outside the low therapy strength range. Likewise, it is possible to set a lower $UL_2$ amplitude for the $LF(A_2)$ stimulation, so that a faint level of paresthesia is felt throughout the therapy strength range, if desired.

The result is a gradation in therapy strength that derives strength of efficacy from a combination of all known pain relief mechanisms and is controllable from a simple, single linear 'strength' based user interface. The patients' perceived stimulation level, via paresthesia, corresponds with their strength setting.

Traditional paresthesia-based spinal cord stimulation (SCS) therapy makes use of dorsal column axon recruitment to induce a tingling sensation overlapping with the region of nociception and thus reducing the perception and experience of pain. Its effect begins in minutes and the paresthesia sensation is typically tolerated by the patient for the continued reduction of their perception of pain. Patients may adjust the stimulation amplitude to a greater level to enhance their pain relief during periods of heighted pain, and may reduce the amplitude and sensation of paresthesia during periods of restfulness, decreased pain, or different body positions which influence lead position relative to the spinal cord. Due to the fact that paresthesia is an unnatural sensation, patients prefer to use this control to minimize it.

The mechanism of action of paresthesia-based stimulation is as follows: Electrical fields generated by SCS leads over the dorsal columns of the spinal cord excite action potentials in axially oriented dorsal column axons, which are associated with conduction of sensory information to the brain. These action potentials propagate to the brain, inducing paresthesia sensations, as well as retrograde into the dorsal horn network of the spinal columnar grey matter. This retrograde propagation reaches excitatory synapses connected from the dorsal column axons to inhibitory interneurons, the excitation of those inhibitory interneurons facilitates inhibition of pain relay neurons.

High frequency SCS therapy utilizes stimulation frequencies between 1 kHz and 100 kHz to achieve a neuromodulatory effect without recruiting the dorsal column fibers associated with paresthesia. Research indicates that this therapy modality reduces the wind-up hypersensitivity of dorsal horn interneurons responsible for relaying a painful sensation from the peripheral to the central nervous system. Pain relief associated with this stimulation may require several hours to a day to take effect.

The mechanism of action of this mode of therapy is still under debate; however the prevailing theory is as follows. High frequency (HF) SCS stimulation has little influence on the dorsal column axons which facilitate paresthesia therapy, instead it directly induces slight potentiation changes on lamina I neurons in the dorsal horn of the spinal cord. The potentiation changes trigger a cascade of intracellular signalling responses which induce a direct inhibition of sensitization and suppression of activity of neuropathic pain relay neurons in the dorsal horn. This approach is similar in frequencies to high frequency (HF) transcutaneous spinal electroanalgesia (TSE) which has been available for decades. Whether the underlying mechanisms and site of pain relief action are the same between HF TSE and HF SCS remains to be determined.

The herein presented invention provides for a new SCS stimulation approach that is designed to permit rapid, easy to use titration to a patient's preference and pain level as well as deliver pain relief by activating all known mechanisms.

Implantable spinal cord stimulators, with associated percutaneous or paddle leads implanted in the supra-dural space in patients' vertebral lumen, are known to those skilled in the art. Those known components and their associated supporting chargers and patient remotes will not be described herein.

The present invention particularly makes use of these components to provide spinal cord stimulation to patients using a plurality of interleaved stimulation pulses of low, paresthesia-inducing frequency, and high frequency, sub-paresthesia inducing stimulation when delivered with an integrated dynamic amplitude program as described. Particularly introduced is a concept of therapy 'strength' whereby the strength represents a setting by the patient that is not directly correlated to the stimulation amplitude of a program as it is in existing SCS devices, but rather is a parameter abstracted such that it refers to the amount of therapy the patient is receiving from a combination of programs that are individually titrated according to strength based on a relationship as described below. Furthermore, the strength parameter space is preferably divided into ranges of low, increasing, and high paresthesia experience. Within the interleaved therapeutic stimulation, pulses are delivered such that a plurality of charge-balanced high frequency (HF) pulses is delivered in the range of 200 Hz-100 kHz at an amplitude $A_1$. These pulses are delivered at substantially the same time as a series of charge-balanced low frequency (LF) pulses in the range of 1 Hz-200 Hz at an amplitude $A_2$. The pulses may be delivered on the same electrodes, with the LF pulses and their charge-balancing phase individually interrupting the delivery of the high frequency (HF) train, or on different electrodes.

Amplitude $A_1$ is limited within a range from lower limit $LL_1$ to upper limit $UL_1$ with $LL_1<UL_1$. Similarly, amplitude $A_2$ is given an operation range $LL_2$ to $UL_2$. According to the disclosed invention, $A_1$ and $A_2$ are calculated from a single user input therapy strength setting S, according to FIG. 1. $LS_1$ is the lower strength setting where the first stimulation train $HF(A_1)$ begins ramping up its amplitude, and $US_1$ is the strength setting whereby the $HF(A_1)$ train reaches its limiting maximum amplitude setting $UL_1$. Likewise, $LS_2$ is the lower strength setting where the second stimulation train $LF(A_2)$ begins ramping up its amplitude, and $US_2$ is the strength setting whereby the $LF(A_2)$ train reaches its limiting maximum amplitude setting $UL_2$. For all valid settings, $LS_1<US_1$ and $LS_2<US_2$.

In this way, the limits are set up to allow one stimulation amplitude to begin ramping before a second stimulation amplitude, corresponding to the perception of paresthesia, indicating to the patient that therapy strength is increasing. The patient may increase or decrease therapy strength at will according to their needs.

Other features which are considered as characteristic for the invention are set forth in the appended claims.

Although the invention is illustrated and described herein as embodied in a device and a method for multi-modality spinal cord stimulation therapy, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
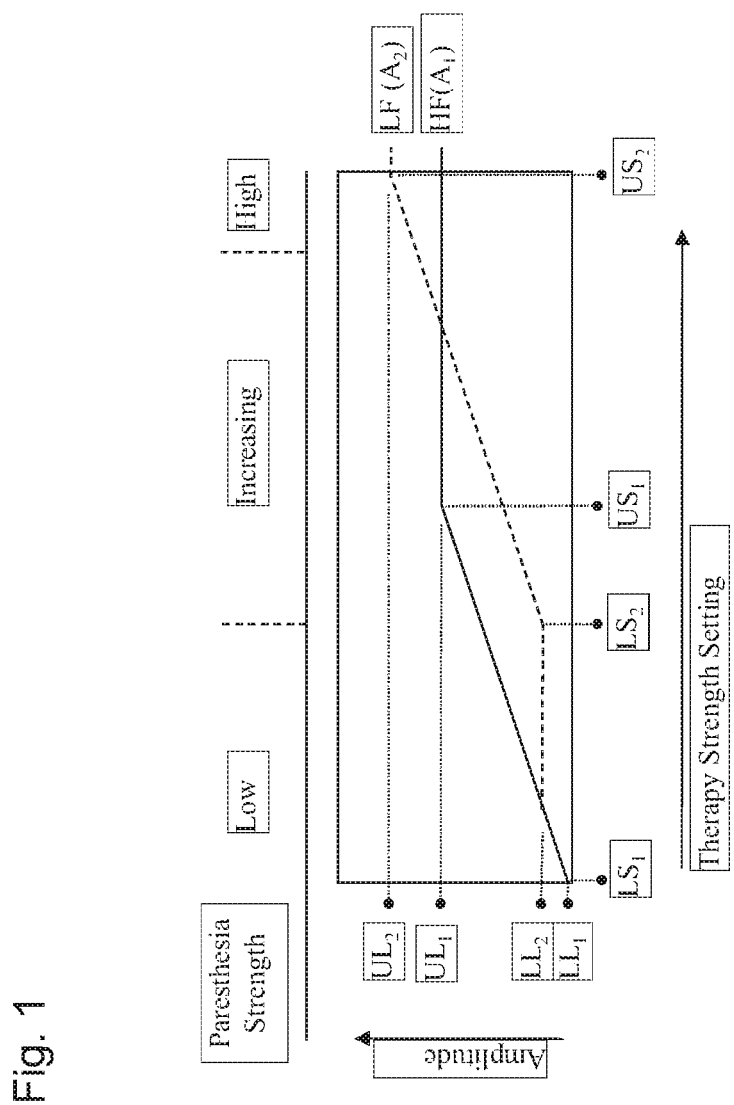
FIG. 1 shows a diagram of the relationship of the user's therapy strength setting according to an embodiment of the invention.

Referring now to the figures of the drawings in detail and first, particularly, to FIG. 1 thereof, there is seen an example according to an embodiment of the invention of a diagram of the relationship of the user's therapy strength setting to stimulation amplitude $A_1$ (high frequency stimulation amplitude) and $A_2$ (low frequency stimulation amplitude).

The process of setting amplitudes relevant to patient therapy is an important aspect of the effectiveness of the herein disclosed invention. This is described as follows:

$UL_1$ is an amplitude limit chosen such that paresthesia is not felt by the patient when this amplitude is reached. Preferably, this amplitude is determined during an initial titration period under clinician guidance such that it also is the amplitude at which the paresthesia-free pain relief mechanism is maximally activated.

Amplitude $UL_2$ is likewise set by a clinician as the maximal amplitude that the patient can comfortably experience paresthesia under low frequency stimulation. This represents a limit whereby the patient is prevented from over-driving their paresthesia stimulation past the point of comfort. This would most commonly be programmed to be reached at $US_2$, the maximal strength setting for the patient.

In a preferred embodiment, $LL_2$ is chosen such that the patient experiences barely-perceptible paresthesia from the low frequency stimulation, and $LL_1$ is chosen such that the therapy is effectively off.

$US_1$ strength setting is chosen to be at a level where further increases of the therapy strength are substantially driven by increases of paresthesia alone. $LS_2$ is chosen to be at a strength level whereby the patient should be experiencing very good daily pain relief, and strength settings above this level are declared to be 'increased paresthesia' strengths to supplement their pain relief as needed.

Figure 2:
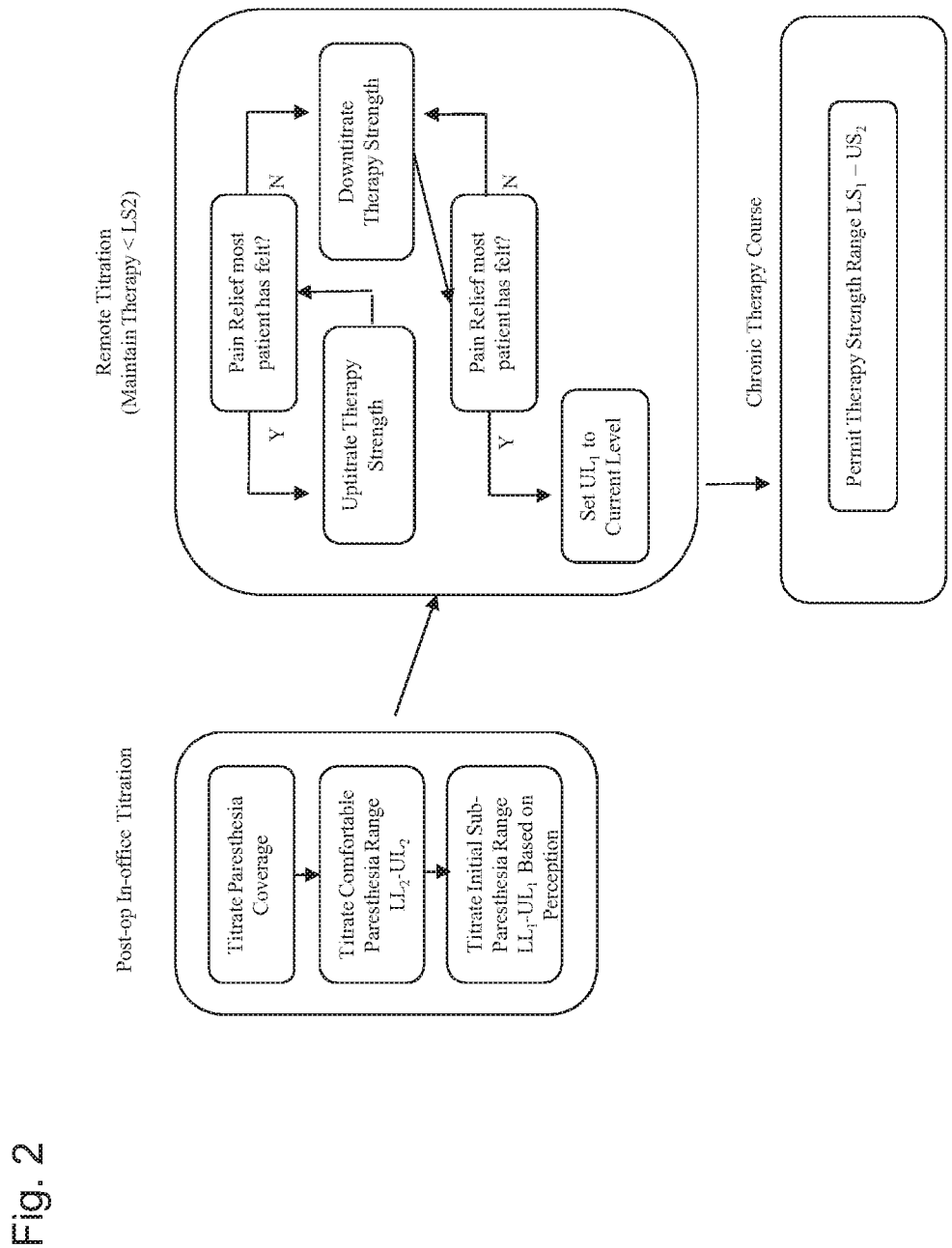
FIG. 2 shows titration strategy for optimizing therapy settings according to an embodiment of the invention.

FIG. 2 shows a titration strategy for optimizing therapy settings to determine the abstracted relationship of therapy strength to programs amplitude output according to an embodiment of the invention.

Figure 3:
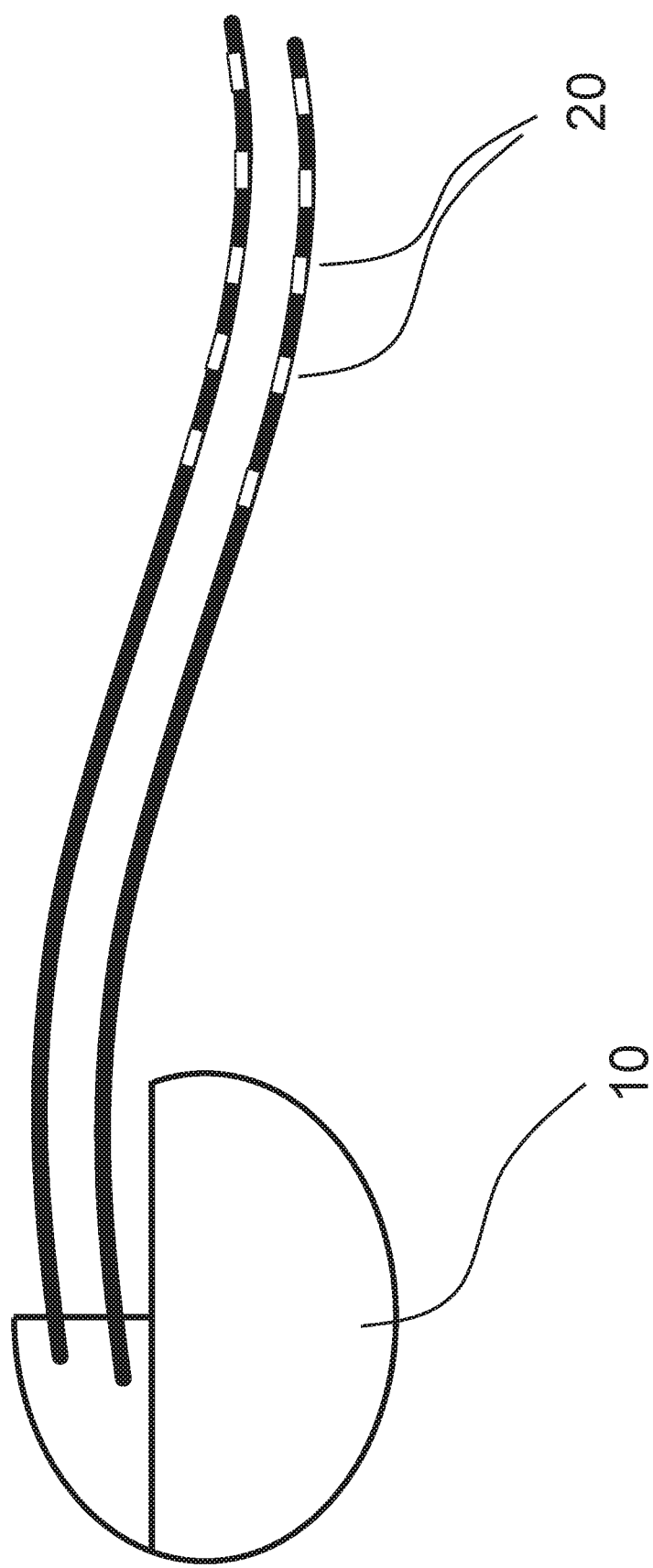
FIG. 3 is a diagrammatic, elevational view of an exemplary implantable pulse generator (IPG) with a first pair of electrodes.

FIG. 3 shows an exemplary implantable pulse generator (IPG) 10 with a first pair of electrodes 20.

The present invention describes a novel SCS therapeutic stimulation approach which delivers pain relieving neuromodulation covering both scientifically studied mechanisms of action and with an intelligent, abstracted program mixing function permitting simple use and feedback tuned to the patient's need.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. A device for neurostimulation, the device comprising:
   a pulse generator capable of generating current having pulses; and
   at least one first pair of electrodes connected to said pulse generator;
   the device providing at least one current parameter configuration for neurostimulation stored in the device;
   said current parameter configuration being programmable by a user;
   said current parameter configuration being associated with a level paresthesia sensation of a patient, when said neurostimulation is performed by using said current parameter configuration;

said current parameter configuration including parameters for a first pulse train and a second pulse train;

said first pulse train having pulse amplitudes within a first range, and said second pulse train having pulse amplitudes within a second range;

said second range having a lower limit set in said current parameter configuration allowing the patient to experience minimal paresthesia at a barely-perceptible level;

said second range having an upper limit set in said current parameter configuration allowing the patient to comfortably experience paresthesia at a maximum comfortable level; and said second range being set to produce a perceptible paresthesia in the patient throughout said second range, from said lower limit to said upper limit.

2. The device according to claim 1, wherein the device is implantable.

3. The device according to claim 1, wherein said at least one first pair of electrodes are constructed as percutaneous leads or paddle leads.

4. The device according to claim 1, wherein said current parameter configuration includes parameters for a first pulse train and a second pulse train, said first pulse train includes high frequency pulses having a frequency in a range of 200 Hz to 100 kHz, and said second pulse train includes low frequency pulses having a frequency in a range of 1 Hz to 200 Hz.

5. The device according to claim 1, wherein said first pulse train includes high frequency pulses having a frequency in a range of 200 Hz to 20 kHz, and said second pulse train includes low frequency pulses having a frequency in a range of 1 Hz to 200 Hz.

6. The device according to claim 1, wherein:

said current parameter configuration includes a therapy strength scale adjustable by the user or by a patient;

at a beginning of said therapy strength scale, said first pulse train is set on a first amplitude at a lower limit of said first range and said second pulse train is set on a second amplitude at a lower limit of said second range;

at an end of said therapy strength scale, said first amplitude is set on an upper limit of said first range, and said second amplitude is set on an upper limit of said second range;

in a low strength range of said therapy strength scale, said second amplitude is maintained, and said first amplitude increases towards or up to said upper limit of said first range;

in a high strength range of said therapy strength scale, said first amplitude is maintained at said upper limit of said first range, while said second amplitude is increased up to said upper limit of said second range; and an increase on said therapy strength scale within or outside of said high strength range can be experienced by the patient as increasing paresthesia.

7. The device according to claim 6, wherein:

said therapy strength scale includes an intermediate therapy strength range between said low and high strength ranges of said therapy strength scale;

said first amplitude increases towards said upper limit of said first range and said second amplitude increases towards said upper limit of said second range; and an increase in said intermediate range can be experienced by the patient as increasing paresthesia.

8. The device according to claim 4, wherein said first and second pulse trains are alternatingly delivered to the patient by said at least one first pair of electrodes.

9. The device according to claim 4, which further comprises a second pair of electrodes connected to said device.

10. The device according to claim 9, wherein said first impulse train is delivered to the patient by said first pair of electrodes, and said second pulse train is delivered to the patient by said second pair of electrodes.

11. The device according to claim 10, wherein said first and second pulse trains are delivered simultaneously.

12. A method for neurostimulation or pain relief, the method comprising the following steps:

applying a current to a patient;

providing the current with:
a first pulse train having high frequency pulses, with a first amplitude in a first range; and
a second pulse train having low frequency pulses with a second amplitude in a second range; and applying the current pulses with an adjustable therapy strength, wherein:
at a lowest strength, the first amplitude is set on a lower limit of the first range, and the second amplitude is set on a lower limit of the second range;
at a highest strength, the first amplitude is set on an upper limit of the first range, and the second amplitude is set on an upper limit of the second range;
in the low strength range, the second amplitude is maintained at the lower limit of the second range, and the first amplitude increase towards or up to the upper limit of the first range;
in the high strength range, the first amplitude is maintained at the upper limit of the first range, while the second amplitude is increased up to the upper limit of the second range;
setting the lower limit of the second range to allow the patient to experience minimal paresthesia at a barely-perceptible level; and
setting the upper limit of the second range to allow the patient to comfortably experience paresthesia at a maximum comfortable level, the second range being set to produce a perceptible paresthesia in the patient throughout the second range, from the lower limit to the upper limit.

13. The method according to claim 12, wherein in an intermediate therapy strength range between the low and high strength ranges, the first amplitude increases towards the upper limit of the first range and the second amplitude increases towards the upper limit of the second range.

14. The method according to claim 12, wherein the therapy strength is adjusted by the patient.

15. The method according to claim 14, wherein at least one of a therapy strength increase within the high strength range or the intermediate strength range is experienced by the patient as increasing paresthesia.

16. The method according to claim 12, which further comprises using an implanted pulse generator to apply the current pulses.

17. The method according to claim 12, which further comprises:

determining the first range and the second range based on an experience of the patient; and setting the first range or the upper limit such that the patient does not experience paresthesia.

* * * * *